United States Patent
Hyun et al.

(10) Patent No.: US 10,765,583 B2
(45) Date of Patent: Sep. 8, 2020

(54) WEARABLE WALKING ASSIST ROBOT AND METHOD FOR CONTROLLING THE SAME

(71) Applicant: Hyundai Motor Company, Seoul (KR)

(72) Inventors: Dong Jin Hyun, Gyeonggi-do (KR);
Kyung Mo Jung, Gyeonggi-do (KR);
Sang In Park, Gyeonggi-do (KR);
Hyun Seop Lim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 589 days.

(21) Appl. No.: 15/280,155

(22) Filed: Sep. 29, 2016

(65) Prior Publication Data
US 2017/0333278 A1    Nov. 23, 2017

(30) Foreign Application Priority Data
May 19, 2016 (KR) .................. 10-2016-0061605

(51) Int. Cl.
*A61H 3/00* (2006.01)
*A61H 1/02* (2006.01)
*A61F 2/72* (2006.01)

(52) U.S. Cl.
CPC .............. *A61H 3/00* (2013.01); *A61F 2/72* (2013.01); *A61H 1/024* (2013.01); *A61H 1/0244* (2013.01); *A61H 2201/164* (2013.01); *A61H 2201/165* (2013.01); *A61H 2201/5015* (2013.01); *A61H 2201/5061* (2013.01); *A61H 2201/5074* (2013.01)

(58) Field of Classification Search
CPC ........ A61H 3/00; A61H 1/024; A61H 1/0244; A61H 2205/10; A61H 2003/007; A61H 3/008; A61F 2/72; A61F 2/68; A61F 2002/6818; B25J 9/0006
See application file for complete search history.

(56) References Cited

U.S. PATENT DOCUMENTS 6,770,045 B2 *   8/2004  Naft ................... A61F 5/0125
                                                                 600/592
7,410,471 B1 *   8/2008  Campbell ............ A61B 5/6829
                                                                 602/16
(Continued)

FOREIGN PATENT DOCUMENTS

KR    10-2005-0088695 A    9/2005
KR       10-0835361 B1     6/2008
(Continued)

*Primary Examiner* — Alvin J Stewart
(74) *Attorney, Agent, or Firm* — Mintz Levin Cohn Ferris Glovsky and Popeo, P.C.; Peter F. Corless

(57) ABSTRACT

A wearable walking assist robot is provided that ensures high walking assistance performance without a complex calculation process by detecting a gait phase based on pressure distribution on feet and performing a corresponding control mode that is set in advance. The wearable walking assist robot includes a sensor unit that senses pressure on the soles of the feet of a wearer and a controller that determines gait phases of both a first leg to be operated and a second leg based on the sensed pressure. Additionally, the controller selects one of a plurality of control modes set in advance based on the determined gait phases and operates a joint-driving unit for the first leg to be operated.

24 Claims, 7 Drawing Sheets

(56) References Cited

U.S. PATENT DOCUMENTS

| | | | | |
|---|---|---|---|---|
| 7,426,873 B1* | 9/2008 | Kholwadwala | A43B 3/00 | 73/777 |
| 8,323,354 B2* | 12/2012 | Bedard | A61F 2/66 | 623/47 |
| 9,456,918 B2* | 10/2016 | Siegler | A61F 5/0127 | |
| 9,526,636 B2* | 12/2016 | Bedard | A61F 2/66 | |
| 9,566,706 B2* | 2/2017 | Yoon | B25J 9/0006 | |
| 9,572,537 B2* | 2/2017 | Sunaoshi | A61B 5/743 | |
| 9,649,206 B2* | 5/2017 | Bedard | A61F 2/644 | |
| 9,707,104 B2* | 7/2017 | Clausen | A61F 2/68 | |
| 9,782,275 B2* | 10/2017 | Shin | A61F 2/60 | |
| 2002/0183673 A1* | 12/2002 | Naft | A61F 5/0125 | 602/16 |
| 2006/0270950 A1* | 11/2006 | Dariush | B25J 9/0006 | 601/5 |
| 2007/0056592 A1* | 3/2007 | Angold | A61H 3/00 | 128/845 |
| 2007/0123997 A1* | 5/2007 | Herr | A61F 2/60 | 623/27 |
| 2008/0039756 A1* | 2/2008 | Thorsteinsson | A61B 5/1038 | 602/23 |
| 2008/0139968 A1* | 6/2008 | Endo | A61B 5/04888 | 600/595 |
| 2008/0167580 A1* | 7/2008 | Avni | A43B 3/0005 | 600/587 |
| 2009/0030530 A1* | 1/2009 | Martin | A61F 2/6607 | 623/53 |
| 2010/0094185 A1* | 4/2010 | Amundson | A61F 5/0102 | 602/16 |
| 2010/0125229 A1* | 5/2010 | Rudolph | A61B 5/1038 | 602/16 |
| 2010/0152629 A1* | 6/2010 | Haas, Jr. | A61B 5/1038 | 601/34 |
| 2010/0262044 A1* | 10/2010 | Siegler | A61B 5/1036 | 600/592 |
| 2010/0324698 A1* | 12/2010 | Sverrisson | A61B 5/1038 | 623/24 |
| 2011/0112447 A1* | 5/2011 | Hsiao-Wecksler | A61H 1/0266 | 601/33 |
| 2011/0257764 A1* | 10/2011 | Herr | A61F 2/60 | 623/24 |
| 2011/0264015 A1* | 10/2011 | Endo | A61H 1/0255 | 601/35 |
| 2012/0172770 A1* | 7/2012 | Almesfer | B25J 9/0006 | 601/35 |
| 2012/0226210 A1* | 9/2012 | Normandin | A43B 7/142 | 602/23 |
| 2012/0271207 A1* | 10/2012 | Schoen | A61F 5/0102 | 601/34 |
| 2012/0289870 A1* | 11/2012 | Hsiao-Wecksler | A61H 1/0266 | 601/5 |
| 2013/0165817 A1* | 6/2013 | Horst | A61F 5/0102 | 600/587 |
| 2013/0171599 A1* | 7/2013 | Bleich | A61B 5/0456 | 434/247 |
| 2013/0190669 A1* | 7/2013 | Rokosz | A61F 5/0125 | 602/16 |
| 2013/0310979 A1* | 11/2013 | Herr | B62D 57/032 | 700/258 |
| 2015/0025423 A1* | 1/2015 | Caires | A61H 1/024 | 601/35 |
| 2015/0045703 A1* | 2/2015 | Strausser | A61H 3/00 | 601/35 |
| 2015/0196403 A1* | 7/2015 | Kim | A61F 2/70 | 623/24 |
| 2015/0297934 A1* | 10/2015 | Agrawal | A61H 1/0266 | 482/4 |
| 2015/0374573 A1* | 12/2015 | Horst | A61H 3/00 | 602/16 |
| 2017/0049587 A1* | 2/2017 | Herr | A61F 5/0123 | |
| 2017/0333278 A1* | 11/2017 | Hyun | A61H 1/024 | |
| 2017/0360644 A1* | 12/2017 | Hyun | A43B 3/0005 | |
| 2018/0160946 A1* | 6/2018 | MacKo | A61B 5/4595 | |
| 2018/0177667 A1* | 6/2018 | Uemura | A61H 3/00 | |
| 2018/0192922 A1* | 7/2018 | Boucher | A61B 5/6828 | |
| 2018/0325713 A1* | 11/2018 | Gregg | A61H 3/00 | |
| 2018/0325766 A1* | 11/2018 | Arzanpour | A61B 5/04888 | |
| 2019/0029914 A1* | 1/2019 | Polygerinos | A61H 3/00 | |
| 2020/0129314 A1* | 4/2020 | Herr | A61F 2/6607 | |

FOREIGN PATENT DOCUMENTS

| | | |
|---|---|---|
| KR | 2009-0104398 A | 10/2009 |
| KR | 10-1317354 B1 | 10/2013 |
| KR | 10-1517058 B1 | 5/2015 |

* cited by examiner

WEARABLE WALKING ASSIST ROBOT AND METHOD FOR CONTROLLING THE SAME

CROSS REFERENCE TO RELATED APPLICATION

The present application claims priority to Korean Patent Application No. 10-2016-0061605, filed May 19, 2016, the entire contents of which is incorporated herein for all purposes by this reference.

BACKGROUND

Field of the Invention

The present invention relates to a wearable walking assist robot and a method for controlling the same and, more particularly, to a wearable walking assist robot that ensures high walking assistance performance without a complex calculation process by detecting a gait phase based on pressure distribution on feet and performing a corresponding control mode that is set in advance, and a method for controlling the wearable walking assist robot.

Description of the Related Art

In general, robots with legs for walking such as a walking assist robot have different dynamics when legs come in contact with the ground, which has been discussed in the name of hybrid dynamics. A technology of determining a gait phase is important for walking robots to process the dynamics of the legs which depends on the gait phases. However, the technologies that have been developed to determine gait phases in the related art divide gait phases into several steps for precise control and use complex algorithms as well to determine gait phases. A complex process of determining gait phases causes the control of robot legs to also be complex and thus, the complex algorithms for determining gait phases are merely theoretically explained and have not been verified in terms of effectiveness that they can be actually applied to robots and can control walking of the robots.

The foregoing is intended merely to aid in the understanding of the background of the present invention, and is not intended to mean that the present invention falls within the purview of the related art that is already known to those skilled in the art.

SUMMARY

Accordingly, the present invention provides a wearable walking assist robot that ensures high walking assistance performance without a complex calculation process by detecting a gait phase of legs through a simplified algorithm based on pressure distribution on feet and selectively controlling one of a plurality of simple control modes in accordance with the gait phase, and a method for controlling the wearable walking assist robot.

According to one aspect of the present invention, a wearable walking assist robot may include: a sensor unit configured to sense pressure on the soles of the feet of a user; and a controller configured to determine gait phases of both a leg to be operated and the other leg based on the pressure sensed by the pressure sensor unit, select one of a plurality of control modes set in advance based on the determined gait phases, and operate a joint-driving unit for the leg to be operated.

The pressure sensor unit may include a plurality of pressure sensors configured to detect pressure applied to the toes and the heels of the soles. The controller may be configured to determine that the toes and the heels are in contact with the ground when pressure applied to the toes and the heels is greater than a predetermined threshold, and determine that the toes and the heels are not in contact with the ground when the pressure is less than the threshold. The controller may further be configured to determine the gait phases by combining a ground-contact state and a non-ground-contact state of the toe and the heel of the leg to be operated with a ground-contact state and a non-ground-contact state of the toe and the heel of the other leg.

Additionally, the controller may be configured to determine as a gait phase that a corresponding leg is supported on the ground throughout the sole when the toe is in contact with the ground and the heel is in contact with the ground, determine as a gait phase that a corresponding leg is supported on the toe on the ground when the toe is in contact with the ground and the heel is not in contact with the ground, determine as a gait phase that a corresponding leg is supported on the heel on the ground when the toe is not in contact with the ground and the heel is in contact with the ground, and determine as a gait phase that a corresponding leg is in the air when both the toe and the heel are not in contact with the ground.

The controller may further be configured to determine one of a weight bearing mode, a compensation of mechanical impedance mode, a ground impact absorbing mode, a ground impact absorbing & extension of virtual leg mode, a pushing ground mode, and a ready for swing phase mode, as a control mode for the leg to be operated based on the gait phases of both the leg to be controlled and the other leg. The weight bearing mode may be a mode in which the controller may be configured to operate the joint-driving unit to push the wearer in a gravity direction with a predetermined force. The compensation of mechanical impedance mode may be a mode in which the controller may be configured to operate the joint-driving unit to compensate for friction at the joints and weight of the robot due to the gravity.

Further, the ground impact absorbing mode may be a mode in which the controller may be configured to generate a virtual spring-damper in a longitudinal direction of a line connecting hip joint and an end of the leg to each other of the walking assist robot and operate the joint-driving unit, using impedance control to make the leg of the robot absorb shock from the outside. The ground impact absorbing & extension of virtual leg mode may be a mode in which the controller may be configured to set a balance point in a impedance control direction for the virtual legs as 0 degree and operate the joint-driving unit to cause the virtual leg to be pulled to be vertically erected while generating a virtual spring-damper in a longitudinal direction of a line connecting a hip joint and the end of the leg to each other of the walking assist robot and operating the joint-driving unit, using impedance control to make the leg of the robot absorb shock from the outside.

The pushing ground mode may be a mode in which the controller may be configured to operate the joint-driving unit to push the end of the leg to be controlled in −x and −y directions in a rectangular coordinate system (e.g., a front direction of the robot is +x direction and a direction vertically going away from the ground is +y direction in the rectangular coordinate system). The ready for swing phase mode may be a mode in which the controller may be configured to operate the joint-driving unit to push the end of the leg to be controlled in +x and +y directions in a rectangular coordinate system for easier swing of the leg (e.g., a front direction of the robot is +x direction and a direction vertically going away from the ground is +y direction in the rectangular coordinate system). When the control mode changes, the controller may be configured to apply a transition parameter, which changes from 0 to 1 along a sinusoidal path for a predetermined time interval, to adjust torque applied to the joint-driving unit in a previous mode and to adjust torque to be applied to the joint-driving unit in a new changed control mode.

According to another aspect of the present invention, a method for controlling a wearable walking assist robot may include: sensing pressure on the soles of the feet of a wearer by a pressure sensor unit; and determining, by a controller, gait phases of both a leg to be operated and the other leg based on the pressure sensed by the pressure sensor unit; and selecting one of a plurality of control modes set in advance based on the determined gait phases, and operating a joint-driving unit of the leg to be. The operating of a joint-driving unit may include: determining whether the control mode changes; and when the control mode changes, applying a transition parameter, which changes from 0 to 1 along a sinusoidal path for a predetermined time interval, to adjust torque applied to the joint-driving units in a previous mode and to adjust torque to be applied to the joint-driving units in a new changed control mode.

As described above, according to the walking assist robot and the control method thereof of various exemplary embodiments of the present invention, it may be possible to more simply determine the gait phases of both a leg to be operated and the other leg in accordance with the load applied to the toe and the heel of the feet. Further, determined gait phases and predetermined walking modes may be matched and then legs may be operated and thus, it may be possible to ensure improved walking assistance performance without a complex calculation process. According to the walking assist robot and the control method thereof of various exemplary embodiments of the present invention, since it may be possible to determine walking assistant force through Jacobian transform regardless of the number of axes, the applicable range is wide.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present invention may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/of" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Wearable walking assist robots and methods of controlling the wearable walking assist robot according to various exemplary embodiments of the present invention will be described hereafter with reference to the accompanying drawings.

Figure 1:
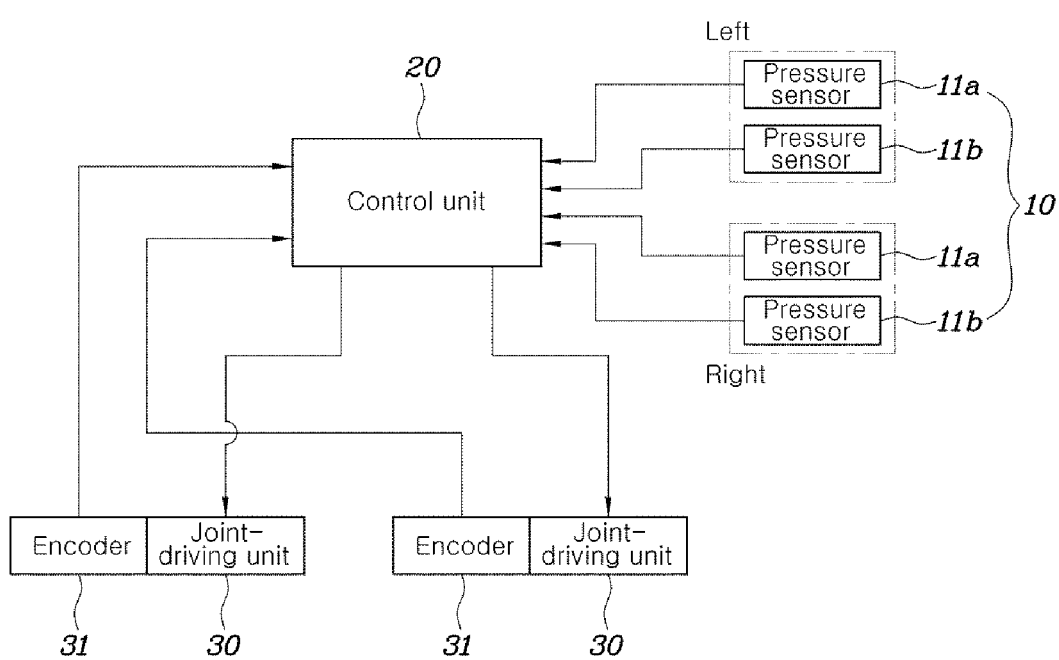
FIG. 1 is a block diagram illustrating a wearable walking assist robot according to an exemplary embodiment of the present invention.

FIG. 1 is a block diagram illustrating a wearable walking assist robot according to an exemplary embodiment of the present invention. Referring to FIG. 1, a wearable walking assist robot according to an exemplary embodiment of the present invention may include a pressure sensor unit 10 configured to sense pressure on the soles of feet of a user (e.g., on an underside on a bottom of a shoe) and a controller 20 configured to determine gait phases of both a leg to be operated and the other leg (e.g., a first and second leg) based on the pressure sensed by the pressure sensor unit 10, select one of a plurality of control modes set in advance based on the determined gait phases, and operate a joint-driving unit 30 for the leg to be operated.

Figure 2A:
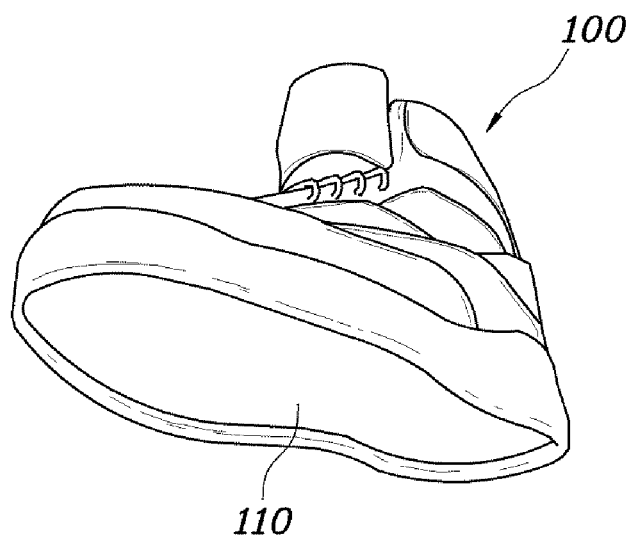
FIGS. 2A and 2B are views showing a pressure sensor unit for a wearable walking assist robot according to an exemplary embodiment of the present invention.
Figure 2B:
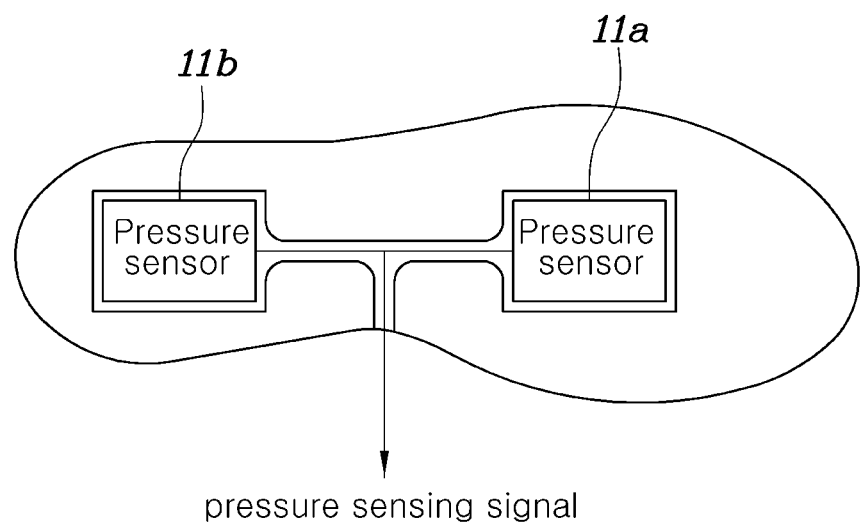

FIGS. 2A and 2B are views showing a pressure sensor unit for a wearable walking assist robot according to an exemplary embodiment of the present invention; As shown in FIGS. 2A and 2B, the pressure sensor unit 10 applied to the wearable walking assist robot according to an exemplary embodiment of the present invention may include a plurality pressure sensors 11a and 11b disposed on the bottom of a shoe (e.g., on the sole of a shoe) to detect pressure applied to the sole. In an exemplary embodiment of the present invention, the pressure sensor unit 10 may include a first pressure sensor 11a positioned proximate to the toe and a second pressure sensor 11b positioned proximate to the heel. The arrangement of the pressure sensor unit 10 may be applied to both feet of the robot wearer. The exemplary embodiment shown in FIGS. 2A and 2B is an example illustrating two pressure sensors 11a and 11b are attached to a shoe of a robot wearer, but various modifications may be considered, for example, three or more pressure sensors may be applied or pressure sensors may be disposed on a sole support member of a robot instead of the shoe of a robot wearer.

Moreover, the controller 20 may be configured to receive signals from the pressure sensor unit 10 that senses pressure on both soles of a robot wearer, determine gait phases of both a first leg to be operated and a second leg based on the sensed pressure, select one of a plurality of control modes set in advance based on the determined gait phases, and operate the joint-driving unit of the leg to be operated. In particular, the controller 20 may be configured to receive signals from the pressure sensor unit 10 configured to sense the pressure on both soles and determine gait phases of the legs in accordance with to which one of the toe and the heel of the soles pressure is applied. For example, the portion to which pressure is applied may be the toe and/or the heel of a foot, and thus, the controller 20 may be configured to determine gait phases of both a leg in a total of four cases for one sole.

Further, the controller 20 may be configured to operate the joint-driving units of the robot (e.g., one unit for each leg) based on the gait phases determined for the legs. Accordingly, the controller 20 may be configured to maintain controls modes for the gait phases of both the first leg to be operated and the second leg, and select control modes for the gait phases of both the first leg to be operate and the second leg and operate the joint-driving unit of the first leg to be operate, thereby providing force for assisting walking. The control technique of the controller 20 may be more clearly understood from the following description about the method for controlling a wearable walking assist robot according to various exemplary embodiments of the present invention.

Figure 3:
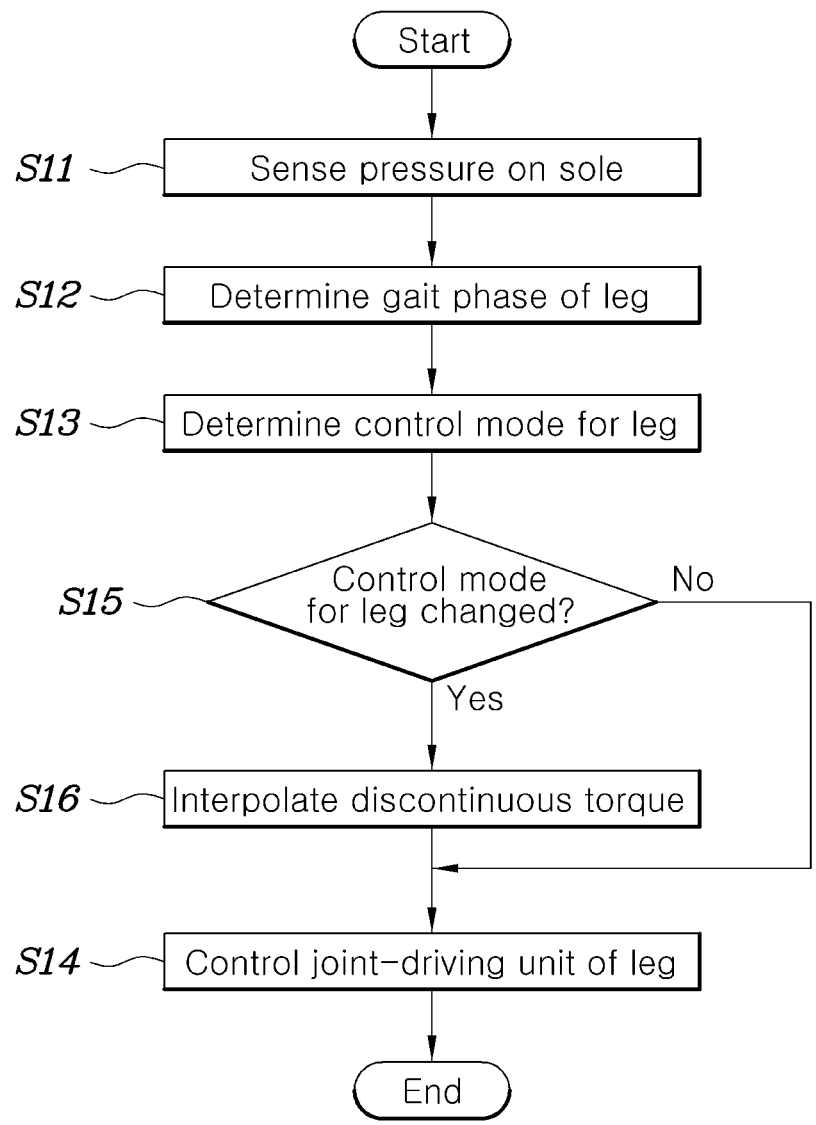
FIG. 3 is a flowchart illustrating a method for controlling a wearable walking assist robot according to an exemplary embodiment of the present invention.

FIG. 3 is a flowchart illustrating a method for controlling a wearable walking assist robot according to an exemplary embodiment of the present invention. Referring to FIG. 3, a method for controlling a wearable walking assist robot according to an exemplary embodiment of the present invention may include: sensing, by a pressure sensor unit 10, pressure applied to the soles of a user (S11); determining, by a controller 20, gait phases of legs based on the sensed pressure (S12); selecting, by the controller 20, one of a plurality of control modes set in advance based on the determined gait phases (S13); and operating, by the controller 20, the joint-driving unit of the leg to be operated (S14).

In other words, one leg is to be operated and the controller may be configured to determine the gait phase of each leg and then the joint-driving unit of the leg that is to be operated may be operated.

First, the sensing of pressure on feet (S11) may include detecting pressure at the toe and the heel of each sole of a user using the pressure sensor unit 10, as described with reference to FIGS. 2A and 2B. For example, a total of four sensing signals may be provided to the controller 20 by two first pressure sensors 11a configured to sense the pressure at the toe of each sole and two second pressure sensors 11b configured to sense the pressure at the heel of each sole.

In the determining of gait phases (S12), the controller 20 may be configured to determine gait phases that correspond to the soles based on the four sensing signals. The following table 1 shows an example that the controller 20 determines gait phases based on the results of sensing pressure on a sole.

TABLE 1

| Gait phase | First pressure sensor (toe) | Second pressure sensor (heel) |
|---|---|---|
| air | non-contact | non-contact |
| heel-strike | non-contact | contact |
| support | contact | contact |
| toe-off | contact | non-contact |

Figure 4:
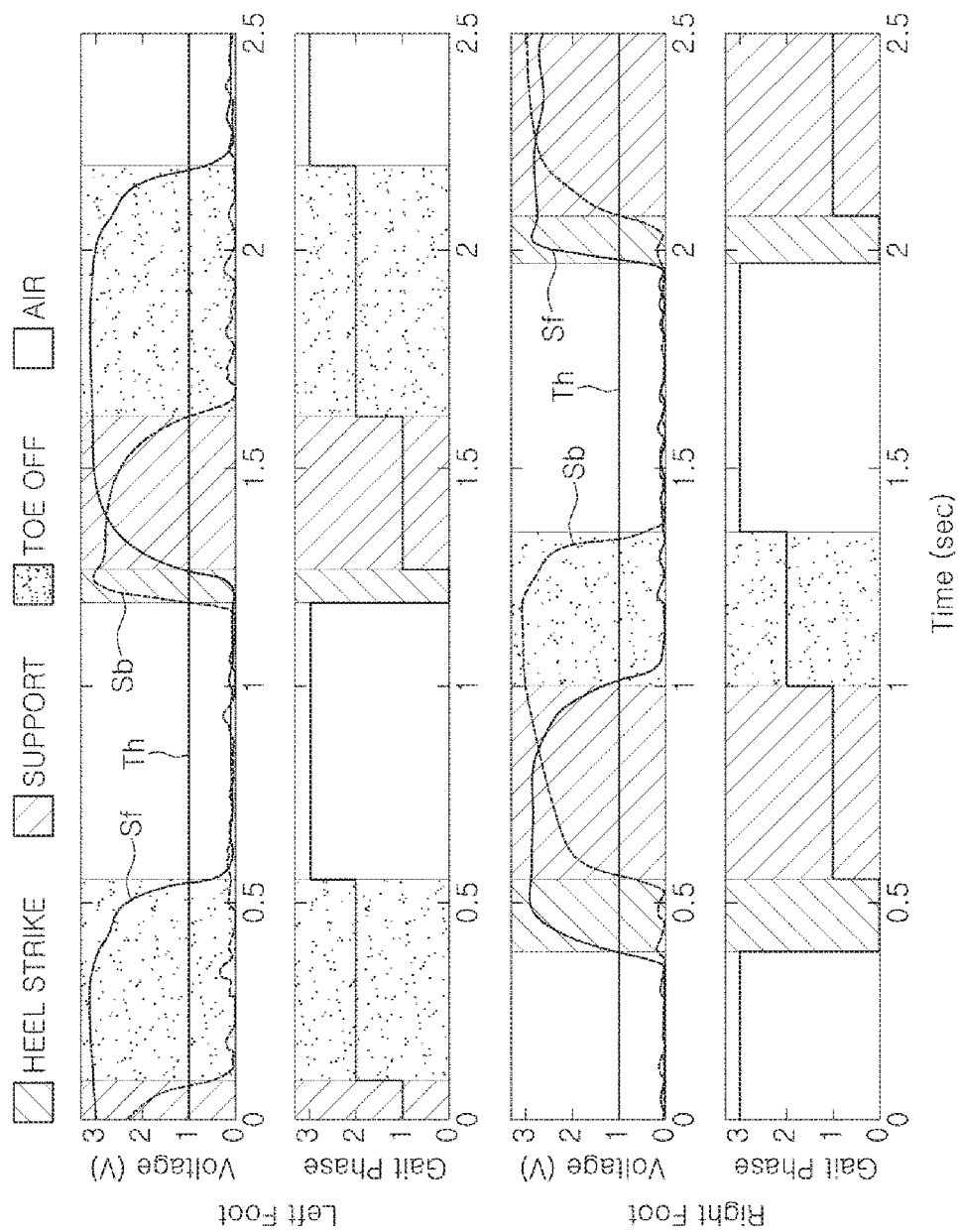
FIG. 4 is a view showing an example of sensing signals from a sensor unit of a wearable walking assist robot according to an exemplary embodiment of the present invention.

As shown in the table, the controller 20 may be configured to determine the gait phases for each leg as an air state, a heel-strike state, a support state, and a toe-off state. Determination of the gait phases may depend on the intensity of the sensing signals from the first pressure sensor 11a and the second pressure sensor 11b and this determination technique is described below with reference to FIG. 4. FIG. 4 is a view showing an example of sensing signals from a sensor unit of a wearable walking assist robot according to an exemplary embodiment of the present invention.

As shown in FIG. 4, the first pressure sensor 11a and second pressure sensor 11b on the left sole and the first pressure sensor 11a and the second pressure sensor 11b on the right sole may be configured to output voltages that correspond to the intensity of sensed pressure as sensing signals. The controller 20 may be configured to compare the intensity of the sensing signals from the pressure sensors with a threshold Th set in advance, determine that the portions corresponding to corresponding sensors are in contact with the ground when the sensing signals are greater than the threshold Th, and determine that the portions (the toe and the heel) corresponding to corresponding pressure sensors are not in contact with the ground when the sensing signals are less than the threshold Th.

Accordingly, the controller 20 may be configured to determine the gait phases of the legs of the soles, as in the table, in accordance with whether the toes and the heels of the feet are in contact with the ground sensed by the first pressure sensors 11a and the second pressure sensors 11b. When the gait phases of the legs are determined, the controller 20 may be configured to determine the control modes for the legs (S13). The controller 20 may then be configured to operate a leg by determining one of a plurality of control modes set in advance, based on the gait phases of both a first leg to be operated and a second leg.

Figure 5:
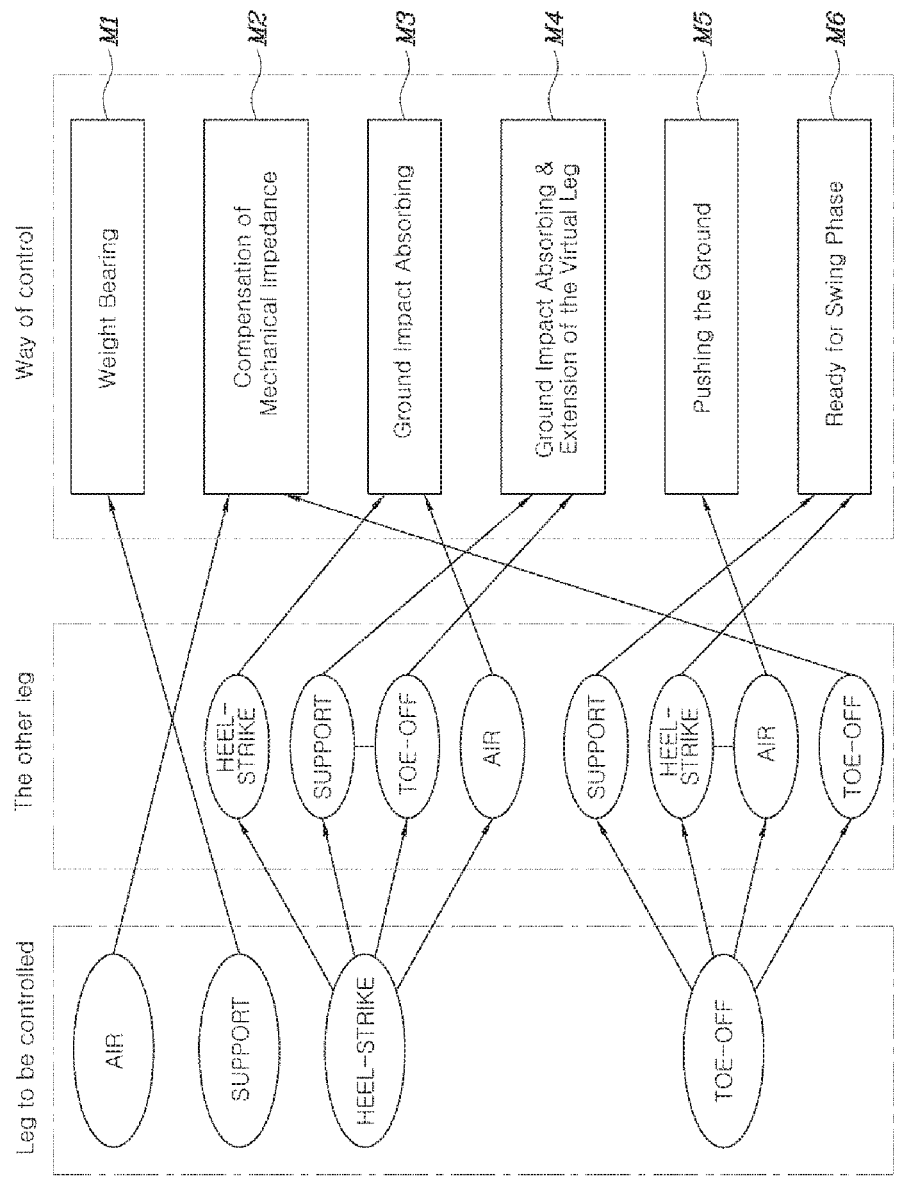
FIG. 5 is a view showing an example of determining control modes on the basis of gait phases of legs in a wearable walking assist robot according to an exemplary embodiment of the present invention.

FIG. 5 is a view showing an example of determining control modes based on gait phases of legs in a wearable walking assist robot according to an exemplary embodiment of the present invention. Referring to FIG. 5, the controller 20 may be configured to select one of a total of six control modes in accordance with the gait phases of both the leg to be operated and the other leg. The six control modes may be determined in advance.

In an exemplary embodiment of the present invention, the six control modes may include a weight bearing mode M1, a compensation of mechanical impedance mode M2, a ground impact absorbing mode M3, a ground impact absorbing & extension of virtual leg mode M4, a pushing ground mode M5, and a ready for swing phase mode M6. For example, when the left leg is in the heel-strike state and the right leg is the support state, the controller 20 may be configured to operate the left leg in the ground impact absorbing & extension of virtual leg mode M4 and the right leg in the weight bearing mode M1.

In an exemplary embodiment of the present invention, when the leg to be operated is in the air state and the support state, the compensation of mechanical impedance mode M2 and the weight bearing mode M1 are determined regardless of the gait phase of the other leg, and in other cases, the control mode may be determined in accordance with the state of the other leg (e.g., the second leg). The weight bearing mode M1 of the six control modes is a mode for adjusting torque of the joint-driving unit (e.g., an actuator) disposed at a joint to push the wearer in the gravity direction (e.g., perpendicularly to the ground) with a desired force set in advance.

For example, a body, thighs, and calves are sequentially connected through joints in common walking assist robots. The body and the thighs are connected through a hip joint-driving unit and the thighs and the calves are connected through a knee-driving unit. An inertia sensor may be disposed on the body, and thus, the pitch angle of the body may be sensed, and an encoder 31 may be disposed at each of the joint-driving units 30, and thus, the rotational angles of the joints may be sensed. The controller 20 may thus be configured to estimate the direction of gravity from the sensing information. The controller 20 may further be configured to create a Jacobian composed of an inertia sensor, a hip joint rotation angle, and a knee joint rotation angle and operate the driving units of the joints to push the ground with a predetermined force in the gravity direction.

Further, the compensation of mechanical impedance mode M2 is provided to compensate for mechanical friction or weight of the walking assist robot. For example, the compensation of mechanical impedance mode M2 is a mode in which the controller 20 may be configured to operate the joint-driving units to compensate for friction at the joints and the weight of links for the body, thighs, and calves. The compensation of mechanical impedance mode M2 is a mode that enables a wearer to more easily move legs without feeling the weight of the legs or friction of the walking assist robot.

The ground impact absorbing mode M3 is a mode for making the legs of the walking assist robot absorb shock from the outside, in which the controller 20 may be configured to generate virtual spring-dampers in the longitudinal directions of virtual legs (e.g., lines from the hip joints to the ends of the robot legs) and operate the driving units for the joints, using impedance control. The virtual legs may be lines from the hip joints to the ends of the legs of the walking assist robot and the controller 20, in the ground impact absorbing mode M3, may be configured to generate virtual spring-dampers in the lines corresponding to the virtual legs, thereby absorbing shock from the outside.

The ground impact absorbing & extension of virtual leg mode M4 is a mode in which the controller 20 may be configured to set a balance point in the impedance control direction for the virtual legs as 0 degree and additionally pull the virtual legs to vertically erect the legs while performing the mode M3. Additionally, the pushing ground mode M5 is a mode performed when the legs are in a delayed stance phase, in which the controller 20 may be configured to push the upper body by operating the driving units for the joints to push the ends of the legs in −x and −y directions (e.g., horizontal directions). Finally, the ready for swing phase mode M6 is a mode in which the controller 20 may be configured to operate the driving units for the joints to push the ends of the legs in +x and +y directions to allow the user to more easily swing the legs.

Figure 6:
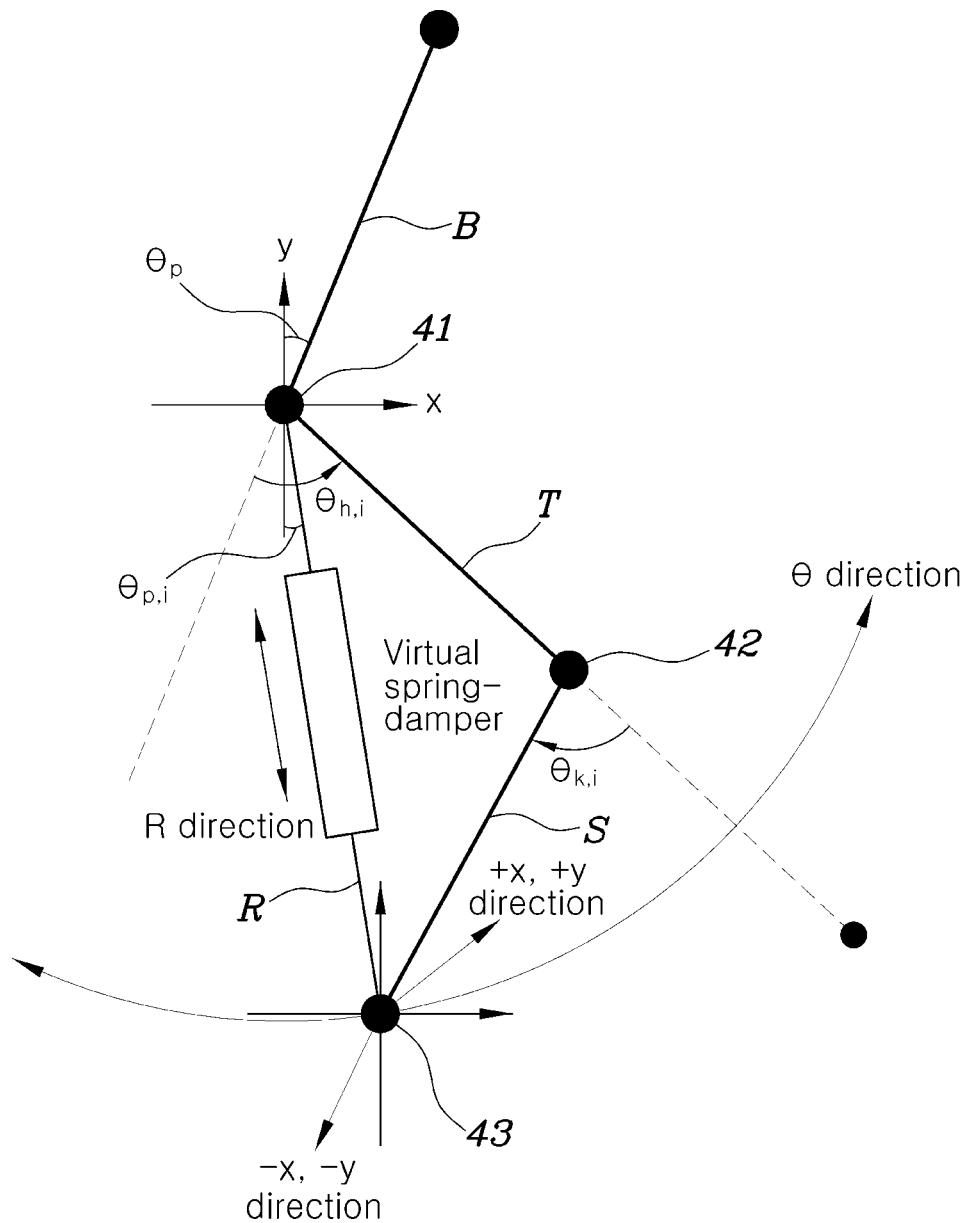
FIG. 6 is a view simply showing an example of a wearable walking assist robot according to an exemplary embodiment of the present invention.

A technique of actually applying the control modes M1 to M6 to the robot is described in more detail hereafter. FIG. 6 is a view simply showing the wearable walking assist robot according to an exemplary embodiment of the present invention, in which the robot may include a body B, a link T for a thigh, a link for a calf, a hip joint 41 connecting the body B and the thigh link T, and a knee joint 42 connecting the thigh link T and the calf link S. The body B may be equipped with an inertial measurement unit (IMU) to sense pitch angles of the body B, while the hip joint 41 and the knee joint 42 may be equipped with a joint-driving unit (for example, an actuator) operated by the controller 20 and an encoder 31 configured to sense the rotational angles of the joints. A pitch angle of the body sensed by the inertial measurement unit and a rotational angle of a joint sensed by the encoder 31 may be provided to the controller 20.

Referring to FIG. 6, the end of a leg may be located with respect to the position of the hip joint in a rectangular coordinate system, as in the following Equation 1.

$$E_{c,i} = \begin{bmatrix} L_1 \sin(\theta_{h,i} - \theta_p) + L_2 \sin(\theta_{h,i} - \theta_p - \theta_{k,i}) \\ -L_1 \cos(\theta_{h,i} - \theta_p) - L_2 \cos(\theta_{h,i} - \theta_p - \theta_{k,i}) \end{bmatrix} \quad \text{Equation 1}$$

wherein $L_1$ is the length of the thigh link T, $L_2$ is the length of the calf link S, $\theta_p$ is the pitch angle of the body B, $\theta_h$ is the rotational angle of the hip joint, and $\theta_k$ is the rotational angle of the knee joint Further, the subscript i indicates the right leg.

Further, the end 43 of a leg may be located in a polar coordinate system as in the following Equation 2, using Equation 1.

$$E_{p,i} = \begin{bmatrix} R_{p,i} \\ \theta_{p,i} \end{bmatrix} = \begin{bmatrix} \sqrt{E_{x,i}^2 + E_{y,i}^2} \\ \tan^{-1} \dfrac{E_{x,i}}{E_{y,i}} \end{bmatrix} \quad \text{Equation 2}$$

A Cartesian Jacobian and a polar Jacobian based on the hip joint may be obtained from Equations 1 and 2, as in the following Equations 3 and 4.

$$J_{c,i} = \dfrac{\partial E_{c,i}}{\partial \bar{q}} \quad \text{Equation 3}$$

$$J_{p,i} = \dfrac{\partial E_{p,i}}{\partial \bar{q}} \quad \text{Equation 4}$$

wherein $\bar{q}$ is the rotational angles of the joints sensed by the encoder 31, which can be expressed as $\bar{q}_i = [\theta_{h,i}\ \theta_{k,i}]^T$.

Accordingly, the speed at the end 43 of the leg may be calculated in a rectangular coordinate system and a polar coordinate system, using the Jacobians, as in the following Equations 4 and 5.

$$\dot{E}_{c,i} = J_{c,i} \begin{bmatrix} \dot{\theta}_{h,i} \\ \dot{\theta}_{k,i} \end{bmatrix} \quad \text{Equation 5}$$

$$\dot{E}_{p,i} = J_{p,i} \begin{bmatrix} \dot{\theta}_{h,i} \\ \dot{\theta}_{k,i} \end{bmatrix} \quad \text{Equation 6}$$

The control modes M1 to M6 may be induced as follows, using the Jacobians induced as described above. The weight bearing mode M1, the pushing ground mode M5, and the ready for swing phase mode M6 may be performed by feedfoward control for directly providing force in the x-axial and/or y-axial direction, so the following Equation 7 may be obtained.

$$\begin{bmatrix} \tau_{h,i} \\ \tau_{k,i} \end{bmatrix} = J_{c,i}^T \begin{bmatrix} F_x \\ F_y \end{bmatrix} \quad \text{Equation 7}$$

In Equation 7, $\tau_{h,i}$ and $\tau_{k,i}$ are torque at the joint-driving units of the hip joint and the knee joint, respectively, $F_x$ are $F_y$ are force set in advance to be applied to the ends of the legs in the weight bearing mode M1, the pushing ground mode M5, and the ready for swing phase mode M6.

For example, force may be applied only in the −y-axial direction in the weight bearing mode M1, so $F_x$ may be 0 and $F_y$ may have a predetermined negative value. Further, force may be applied in the −x and −y directions in the pushing ground mode M5 in the pushing ground mode M5, so $F_x$ and $F_y$ both may have predetermined negative values, while force may be applied in +x and +y directions in the ready for swing phase mode M6, so $F_x$ and $F_y$ both may have predetermined positive values.

Furthermore, the compensation of mechanical impedance mode M2 is a mode in which the controller 20 may be configured to operate the joint-driving units to compensated for friction at the joints or weight due to the gravity and negative feedback may be applied in a rectangular coordinate system. The joints may be operated, as in the following Equation 8, in the ground impact absorbing mode" M3.

$$\begin{bmatrix} \tau_{h,i} \\ \tau_{k,i} \end{bmatrix} = -J_{c,i}^T \begin{bmatrix} 0 & 0 \\ 0 & K_{d,y} \end{bmatrix} \dot{E}_{c,i} \quad \text{Equation 8}$$

wherein $K_{d,y}$ is a virtual constant that is experimentally determined and the unit may be Nsec/deg.

The ground impact absorbing mode M3 is a mode for operating the driving units of the joints under the assumption that there is a virtual spring-damper in the longitudinal direction of each of the lines from the hip joints and the ends of the legs $$\begin{bmatrix} \tau_{h,i} \\ \tau_{k,i} \end{bmatrix} = J_{p,i}^T \left( \begin{bmatrix} K_{p,r} & 0 \\ 0 & 0 \end{bmatrix} \Delta E_{p,i} + \begin{bmatrix} K_{d,r} & 0 \\ 0 & 0 \end{bmatrix} \Delta \dot{E}_{p,i} \right) \quad \text{Equation 9}$$

wherein $K_{p,r}$ and $K_{d,r}$ may be determined in advance in accordance with impedance measured at the legs of the wearer and the units are N/m and Nsec/m, respectively. Further, $\Delta E_{p,i}$ is the difference between the position of the end of a leg in the heel-strike state and the later position of the end of the leg in a polar coordinate system and $\Delta \dot{E}_{p,i}$ is the difference between a stop speed and the speed of the end of a leg in a polar coordinate system.

Additionally, the ground impact absorbing & extension of virtual leg mode M4 is a mode in which the controller M3 may be configured to set a balance point in the impedance control for the virtual legs as 0 degree ($\theta_{p,i}=0$ in FIG. 6) and additionally vertically pull the virtual legs, and the torque at the joint-driving units may be adjusted as in the following Equation 10.

$$\begin{bmatrix} \tau_{h,i} \\ \tau_{k,i} \end{bmatrix} = J_{p,i}^T \left( \begin{bmatrix} K_{p,r} & 0 \\ 0 & 0 \end{bmatrix} \Delta E_{p,i} + \begin{bmatrix} K_{d,r} & 0 \\ 0 & K_{p,\theta} \end{bmatrix} \Delta \dot{E}_{p,i} \right) \quad \text{Equation 10}$$

When $K_{p,\theta}$ is 0 in Equation 10, it becomes Equation 9. In Equation 10, $K_{p,\theta}$ is a value that is not 0 and the unit is N/deg.

Figure 7:
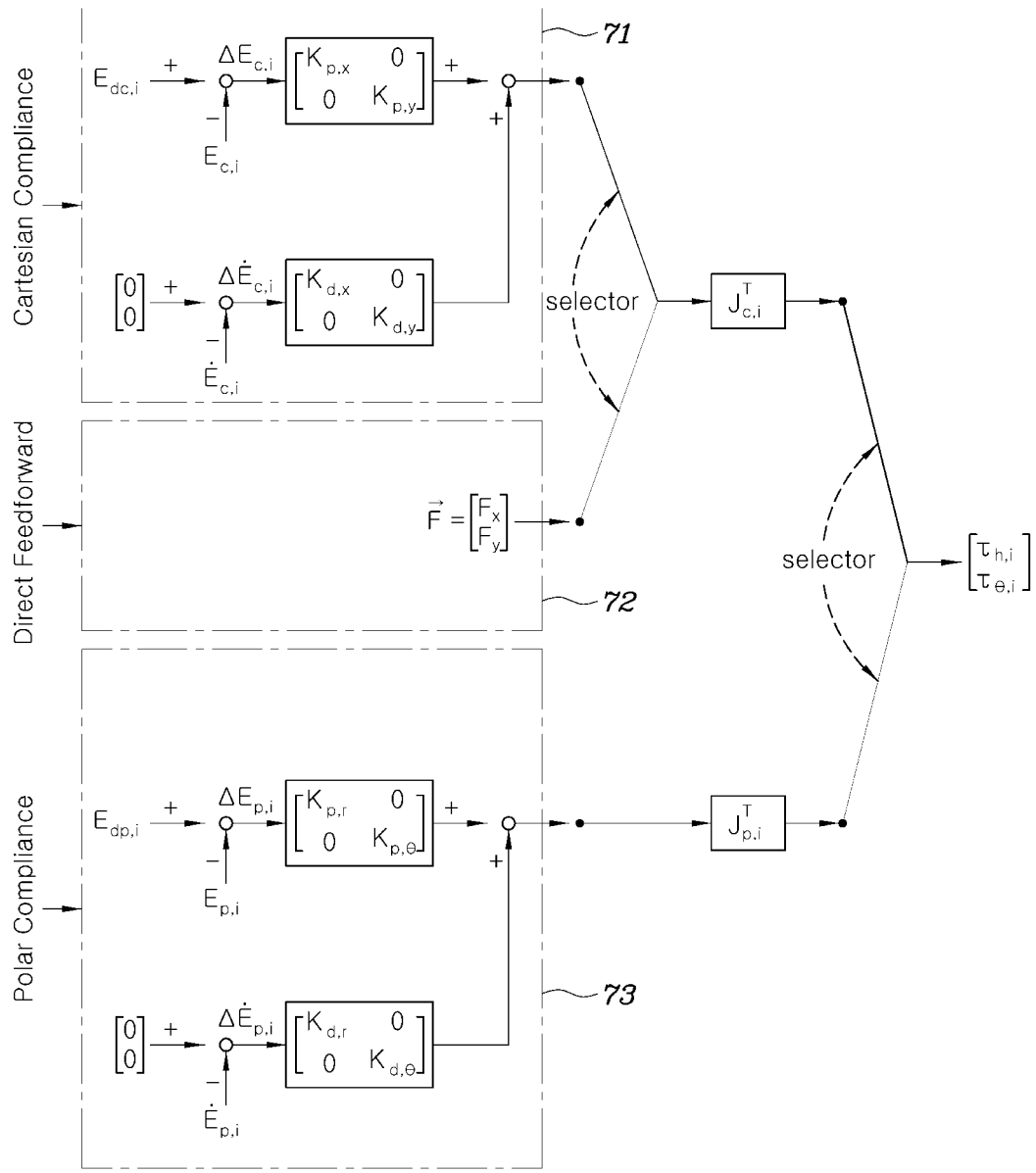
FIG. 7 is a view showing a control technique that is applied to a wearable walking assist robot and a method for controlling the wearable walking assist robot according to an exemplary embodiment of the present invention.

FIG. 7 is a view showing a control technique that is applied to a wearable walking assist robot and a method for controlling the wearable walking assist robot according to an exemplary embodiment of the present invention, in which the impedance control in a rectangular coordinate system indicated by '71' may be applied in the compensation of mechanical impedance mode M2, the direct feedforward control indicated by '72' may be applied in the weight bearing mode M1, the pushing ground mode M5, and the ready for swing phase mode M6, and the impedance control in a polar coordinate system indicated by '73' may be applied in the ground impact absorbing mode M3 and the ground impact absorbing & extension of virtual leg mode M4.

Moreover, an exemplary embodiment of the present invention may determine whether a control mode changes (S15) to prevent a discontinuous section due to a sudden change of torque at the points where control modes change, and when it is determined that a control mode has changed, it may be possible to perform control for interpolating the discontinuous torque of the joints (S16). For the control for interpolating the discontinuous torque that is performed in the step S16, a technique in which a controller 20 applies a transition parameter, which changes from 0 to 1 along a sinusoidal path for a predetermined time interval, to previous control torque and new control torque may be used.

The transition parameter 'p' is expressed as in the following Equation 11 and control torque applied to a transition period using the transition parameter may be expressed as in the Equation 12.

$$p = \sin\left(\frac{\pi}{2} SAT\left(\frac{t}{t_p}, 0, 1\right)\right) \quad \text{Equation 11}$$

$$\begin{bmatrix} \tau_{h,i} \\ \tau_{k,i} \end{bmatrix} = p \begin{bmatrix} \tau_{h,posterior} \\ \tau_{k,posterior} \end{bmatrix} + (1-p) \begin{bmatrix} \tau_{h,prior} \\ \tau_{k,prior} \end{bmatrix} \quad \text{Equation 12}$$

In Equations 11 and 12, $t_p$ is a predetermined time interval and SAT is a saturation function, in which SAT (x, a, b) has the value x for a<x<b, the value a for a <x, and the value b for x<b. Further, $\tau_{h,posterior}$ and $\tau_{k,posterior}$ are control torque at the joint-driving units in the changed control mode and $\tau_{t,prior}$ and $\tau_{k,prior}$ are control toque of the joint-driving units in the previous control mode before changed.

As described above, according to a walking assist robot and a control method thereof of various exemplary embodiments of the present invention, it may be possible to more simply determine the gait phases of both a leg to be operated and the other leg based on load applied to the toe and the heel of the feet. Further, determined gait phases and predetermined walking modes may be matched and then legs may be operated, and thus, it may be possible to ensure improved walking assistance performance without a complex calculation process. According to a walking assist robot and a control method thereof of various exemplary embodiments of the present invention, since it may be possible to determine waling assistant force through simple Jacobian transform regardless of the number of axes, the applicable range is wide.

Although the present invention was described with reference to specific exemplary embodiments shown in the drawings, it is apparent to those skilled in the art that the present invention may be changed and modified in various ways without departing from the scope of the present invention, which is described in the following claims.

What is claimed is:

1. A wearable walking assist robot, comprising:
   a sensor unit configured to sense pressure on the soles of the feet of a user; and
   a controller configured to determine gait phases of both a first leg to be operated and a second leg based on the pressure sensed by the pressure sensor unit, select one of a plurality of control modes set in advance based on the determined gait phases, and operate a joint-driving unit for the first leg to be operated,
   wherein the controller is configured to determine one selected from the group including a ground impact absorbing mode as a control mode for the first leg to be operated based on the gait phases of both the first leg to be operated and the second leg, and
   wherein the ground impact absorbing mode is a mode in which the controller is configured to generate a virtual spring-damper in a longitudinal direction of a line connecting hip joint and an end of the first leg to each other of the walking assist robot and operate the joint-driving unit, using impedance control to make the first leg of the robot absorb shock from the outside.

2. The robot of claim 1, wherein the pressure sensor unit includes a plurality of pressure sensors configured to sense pressure applied to the toes and the heels of the soles.

3. The robot of claim 2, wherein the controller is configured to determine that the toes and the heels are in contact with the ground when pressure applied to the toes and the heels is greater than a predetermined threshold, and determine that the toes and the heels are not in contact with the ground when the pressure is less than the threshold.

4. The robot of claim 3, wherein the controller is configured to determine the gait phases by combining a ground-contact state and a non-ground-contact state of the toe and the heel of the first leg to be operated with a ground-contact state and a non-ground-contact state of the toe and the heel of the second leg.

5. The robot of claim 4, wherein the controller is configured to:
   determine as a gait phase that a corresponding leg is supported on the ground throughout the sole when the toe is in contact with the ground and the heel is in contact with the ground,
   determine as a gait phase that a corresponding leg is supported on the toe on the ground when the toe is in contact with the ground and the heel is not in contact with the ground,
   determine as a gait phase that a corresponding leg is supported on the heel on the ground when the toe is not in contact with the ground and the heel is in contact with the ground, and
   determine as a gait phase that a corresponding leg is in the air when both the toe and the heel are not in contact with the ground.

6. The robot of claim 1, wherein the controller is configured to determine one selected from the group consisting of: a weight bearing mode, a compensation of mechanical impedance mode, a ground impact absorbing mode, the ground impact absorbing and extension of virtual leg mode, a pushing ground mode, and a ready for swing phase mode, as the control mode for the first leg to be operated based on the gait phases of both the first leg to be operated and the second leg.

7. The robot of claim 6, wherein the weight bearing mode is a mode in which the controller is configured to operate the joint-driving unit to push the user in a gravity direction with a predetermined force.

8. The robot of claim 6, wherein the compensation of mechanical impedance mode is a mode in which the controller is configured to operate the joint-driving units to compensate for friction at the joints and weight of the robot due to the gravity.

9. The robot of claim 6, wherein the ground impact absorbing and extension of virtual leg mode is a mode in which the controller is configured to set a balance point in a impedance control direction for the virtual legs as 0 degrees and operate the joint-driving unit to pull the virtual leg to be vertically erected while making a virtual spring-damper in a longitudinal direction of a line connecting a hip joint and the end of the first leg to each other of the walking assist robot and operating the joint-driving unit, using impedance control to make the first leg of the robot absorb shock from the outside.

10. The robot of claim 6, wherein the pushing ground mode is a mode in which the controller is configured to operate the joint-driving unit to push the end of the first leg to be controlled in −x and −y directions in a rectangular coordinate system.

11. The robot of claim 6, wherein the ready for swing phase mode is a mode in which the controller is configured to operate the joint-driving unit to push the end of the first leg to be controlled in +x and +y directions in a rectangular coordinate system for swing of the first leg.

12. The robot of claim 6, wherein when the control mode changes, the controller is configured to apply a transition parameter, which changes from 0 to 1 along a sinusoidal path for a predetermined time interval, to adjust torque applied to the joint-driving units in a previous mode and to adjust torque to be applied to the joint-driving unit in a new changed control mode.

13. A method for controlling a wearable walking assist robot, comprising:
   sensing, by a pressure sensing unit, pressure on the soles of the feet of a user; and
   determining, by a controller, gait phases of both a first leg to be operated and a second leg based on the pressure sensed by the pressure sensor unit; and selecting, by the controller, one of a plurality of control modes set in advance based on the determined gait phases and operating a joint-driving unit of the first leg to be operated, wherein the operating of a joint-driving unit includes determining one selected from the group including a ground impact absorbing mode as a control mode for the first leg to be operated based on the gait phases of both the first leg to be operated and the second leg, and wherein the mode of the first leg to be operated is determined as the ground impact absorbing mode, a virtual spring-damper is generated in a longitudinal direction of a line connecting a hip joint and an end of the first leg to each other of the walking assist robot and the joint-driving unit is operated using impedance control to make the first leg of the robot absorb shock from the outside.

14. The method of claim 13, wherein the sensing of pressure includes sensing pressure applied to the toes and the heels of the soles.

15. The method of claim 14, wherein the determining of gait phases includes determining that the toes and the heels are in contact with the ground when pressure applied to the toes and the heels is greater than a predetermined threshold, and determining that the toes and the heels are not in contact with the ground when the pressure is less than the threshold.

16. The method of claim 15, wherein determining of gait phases includes determining the gait phases by combining a ground-contact state and a non-ground-contact state of the toe and the heel of the first leg to be operated with a ground-contact state and a non-ground-contact state of the toe and the heel of the second leg.

17. The method of claim 16, wherein the determining of gait phases includes:
    determining, by the controller, as a gait phase that a corresponding leg is supported on the ground throughout the sole when the toe is in contact with the ground and the heel is in contact with the ground,
    determining, by the controller, as a gait phase that a corresponding leg is supported on the toe on the ground when the toe is in contact with the ground and the heel is not in contact with the ground,
    determining, by the controller, as a gait phase that a corresponding leg is supported on the heel on the ground when the toe is not in contact with the ground and the heel is in contact with the ground, and
    determining, by the controller, as a gait phase that a corresponding leg is in the air when both the toe and the heel are not in contact with the ground.

18. The robot of claim 13, wherein the operating of a joint-driving unit includes determining one selected from the group consisting of: a weight bearing mode, a compensation of mechanical impedance mode, the ground impact absorbing mode, a ground impact absorbing and extension of virtual leg mode, a pushing ground mode, and a ready for swing phase mode, as the control mode for the first leg to be operated based on the gait phases of both the first leg to be operated and the second leg.

19. The method of claim 18, wherein in the operating of a joint-driving unit, when the mode of the first leg to be operated is determined as the weight bearing mode, the joint-driving unit is operated to push the user in a gravity direction with a predetermined force.

20. The method of claim 18, wherein in the operating of a joint-driving unit, when the mode of the first leg to be operated is determined as the compensation of mechanical impedance mode, the joint-driving unit is operated to compensate for friction at the joint and weight of the robot due to the gravity.

21. The method of claim 18, wherein in the operating of a joint-driving unit, the mode of the first leg to be operated is determined as the ground impact absorbing and extension of virtual leg mode, a balance point is set in a impedance control direction for a virtual leg as 0 degree and the joint-driving unit is operated to pull the virtual leg to be vertically erected while a virtual spring-damper is generated in a longitudinal direction of a line connecting a hip joint and the end of a leg to each other of the walking assist robot and the joint-driving unit is operated using impedance control to make the leg of the robot absorb shock from the outside.

22. The method of claim 18, wherein in the operating of a joint-driving unit, the mode of the first leg to be operated is determined as the pushing ground mode, the joint-driving unit is operated to push the end of the first leg to be operated in −x and −y directions in a rectangular coordinate system.

23. The method of claim 18, wherein in the operating of a joint-driving unit, the mode of the first leg to be operated is determined as the ready for swing phase mode, the joint-driving unit is operated to push the end of the leg in +x and +y direction in a rectangular coordinate system for swing of the first leg to be operated.

24. The method of claim 18, wherein the operating of a joint-driving unit includes:
    determining, by the controller, whether the control mode changes; and
    when the control mode changes, applying, by the controller, a transition parameter, which changes from 0 to 1 along a sinusoidal path for a predetermined time interval to adjust torque applied to the joint-driving units in a previous mode and to adjust torque to be applied to the joint-driving units in a new changed control mode.

\* \* \* \* \*